United States Patent [19]

Lindemann et al.

[11] 4,111,653

[45] Sep. 5, 1978

[54] ALKALI STANNITE DEPILATORIES

[75] Inventors: Martin K. O. Lindemann, Freehold, N.J.; Harvey A. Lazar, Silver Springs, Md.

[73] Assignee: The Gillette Company, Boston, Mass.

[21] Appl. No.: 769,386

[22] Filed: Feb. 16, 1977

[51] Int. Cl.² .......................................... A61K 7/155
[52] U.S. Cl. ...................................................... 8/161
[58] Field of Search .................................. 8/161, 160

[56] References Cited

U.S. PATENT DOCUMENTS

| | | | |
|---|---|---|---|
| 1,899,707 | 2/1933 | McKee et al. | 8/161 |
| 2,123,214 | 7/1938 | Stoddard et al. | 8/161 |
| 2,199,249 | 4/1940 | Stoddard et al. | 8/161 |

OTHER PUBLICATIONS

Sagarin, "Cosmetics — Science & Technology," (1957) published by Interscience Publishers, Inc., N.Y., p. 466. Chemical Abstracts, vol. 83: 84720j, vol. 84: 65185t & vol. 84: 74545n.

*Primary Examiner*—Donald B. Moyer
*Attorney, Agent, or Firm*—Richard A. Wise; R. Danny Huntington

[57] ABSTRACT

Aqueous depilatory compositions are made by complexing 0.2 to 0.8 Sn(II) with a polyhydroxycarboxylate anion having five to seven carbon atoms and four to six hydroxyl groups in a molar ratio from 2:1 to 1:2 at a pH from 12.8 to 13.3.

8 Claims, No Drawings

ALKALI STANNITE DEPILATORIES

FIELD OF THE INVENTION

This invention relates to aqueous alkali stannite systems stabilized by complexing with polyhydroxymonocarboxylate anions. The invention is useful in the preparation of personal care depilatories.

BACKGROUND OF THE INVENTION

Commercial depilatories presently on the market have many negative attributes. One of the worst is the malodor given off by those based on alkaline thioglycolate. Other disadvantages of present depilatory systems include their general messiness and the lengthy processing time which contributes to dermal irritation problems in some users.

The use of essentially odorless, soluble alkali stannite systems as depilatories has been known for some time. However, these systems have suffered from the disadvantage that soluble stannite rapidly decomposes to stannate, Sn(IV) and metallic tin, Sn(O), or reacts in the presence of water to form stannous oxide and alkali metal hydroxide, unless it is stabilized in some manner. Attempts to stabilize stannites utilizing either soluble silicates or certain organic compounds having three or more hydroxyl groups are described in Stoddard and Berlin, U.S. Pat. Nos. 2,123,214, and 2,199,249. These systems suffer from the fact that when stannites are used at pH 12.6 or less, the amount of time required to obtain complete depilation is increased, consequently increasing the possibility of dermal irritation.

We have found that aqueous alkali stannite systems are effectively stabilized by the addition of polyhydroxycarboxylate anions having five to seven carbon atoms and four to six hydroxyl groups. The resulting soluble stannite/acid complex depilates rapidly and effectively in the pH range from 12.8 to 13.3 with substantially no irritation.

DETAILED DESCRIPTION OF THE INVENTION

It has now been found that alkali stannites can be stabilized for longer periods of time and used safely for depilation at a higher pH than previously possible by complexing with polyhydroxymonocarboxylate anions having from five to seven carbon atoms and four to six hydroxyl groups.

While sodium stannite by itself is soluble in aqueous solutions above pH 13, it readily disproportionates to Sn(O) and Sn(IV) even when oxygen is excluded. The methods of stabilization in the prior art all have the general aim of retarding this disproportionation since to be of value commercially, a depilatory must be capable of storage for a year or more.

The active species in the present invention in Sn(II). Any of the various stannous salts such as $SnCl_2$, $SnSO_4$, SnO, $SnBr_2$, or $SnI_2$, can be used to prepare the stabilized stannite solution. However, $SnCl_2.2H_2O$ is preferred because of its solubility and availability. It is possible to form the stabilized stannite solutions of this invention using either of two methods. While both begin with the use of a stannous salt, one goes through the intermediate stop of forming $SnO.xH_2O$. In the first method, the stannous salt is added directly to a solution containing both an alkali metal hydroxide (either sodium or potassium hydroxide) and a complexing polyhydroxycarboxylate anion. In the second method, $SnO.xH_2O$ is first formed and then washed before being added to an alkali metal hydroxide in the same manner as above.

The second method is preferred because one of the steps in depilation is the degradation that accompanies the swelling of the hair due to water absorption. Since salts generally act as deswelling agents, the first procedure above which results in the formation of considerable amounts of the alkali metal salt remaining in solution, yields a mixture somewhate reduced in depilating ability compared to the results of the second procedure. In contrast, the second procedure removes the salt from the system before complexing takes place, thus significantly reducing deswelling.

While it is possible to practice our invention using concentrations of tin between 0.2 and 0.8 M, the preferred range is 0.3 to 0.5 M, with the best results at 0.4 M. Complexes with the tin can be formed in molar ratio of tin to polyhydroxycarboxylate anion from 2:1 to 1:2, preferably 3:2 to 4:3. As the amount of complexing agent increases past the optimum ratio, a decrease in swelling occurs which continues as more complexing agent is added. This may well be due to steric hindrance preventing the complex from entering the hair.

As mentioned above, our compositions depilate most effectively at pH levels higher than taught as useful in the prior art. While the complex formed are stable down to much lower values, degradation of the hair is not apparent below a pH of 12.5. We have found that the pH range over which effective non-irritating depilation takes place is from 12.8 to 13.3, with the preferree range being from 13.0 to 13.1. These pH ranges are achieved by adding alkali metal hydroxides to the previously prepared stannous salt or $SnO.xH_2O$ - polyhydroxycarboxylate anion complex described above.

It is important to note that the pH required for effective depilation increases as the Sn(II) concentration in the solution is increased. While a pH of 13.1 is effective with 0.4 M tin, increasing the tin to 0.7 M requires a pH of at least 13.3 to be as effective.

After the complex has been formed, it may be thickened by mixing with finely ground kaolin or clay, or other conventional thickeners stable at alkaline pH and inert to the substances in the solution, The depilatory is more readily applied after thickening since the viscosity of an unthickened solution is essentially that of water (less than 50 cps). The addition of a thickener (e.g., approximately 20% kaolin) raises the viscosity to about 1700 cps resulting in a cream which is more readily retained on the skin for the requisite length of time than an unthickened solution. The viscosity can be raised as high as 7500 cps, essentially a paste, without hindering depilation.

Another means of enhancing the action of the present invention is by the addition of surfactants. Any anionic, nonionic or ampholytic surfactant which is stable at alkaline pH and inert to the substances of the solution can be used. The following table exemplifies specific surfactants which may be used in conjunction with the practice of our invention but should not be construed as limiting the generality of the principle disclosed herein.

TABLE I

| Anionic Surfactants | Nonionic Surfactants |
|---|---|
| fatty taurates | fatty alkanolamides |
| isethionates | alkoxylated amides |
| sarcosinates | amine oxides |
| alkyl-and arylsulfonates | sorbitan esters |

TABLE I-continued

| | |
|---|---|
| alkyl-arylsulfonates | phosphate esters |
| napthalenesulfonates | fatty esters |
| sulfosuccinates | glycerol fatty esters |
| fatty ester sulfates | fatty alcohols |
| fatty acid sulfates | alkoxylated alcohols |
| alcohol sulfates | alkoxylated fatty acids |
| ethoxylated alcohol sulfates and sulfonates | |
| ethoxylated alkyl-arylphenol sulfates | |
| ethoxylated fatty sulfates | |
| ether sulfates | |
| alkyl and aryl phosphates | |
| salts of fatty acids | |

Ampholytic Surfactants betaines
sulfobetaines
carboxyimidazoles

The following table exemplifies polyhydroxymonocarboxylic acids (which convert to the corresponding carboxylate anion in alkaline solution) that are operable in the practice of our invention but should not be construed as limiting the generality of the principles disclosed herein.

TABLE II

Ribonic acid $$\begin{array}{c} CO_2H \\ | \\ HCOH \\ | \\ HCOH \\ | \\ HCOH \\ | \\ CH_2OH \end{array}$$

Arabonic acid $$\begin{array}{c} CO_2H \\ | \\ HOCH \\ | \\ HCOH \\ | \\ HCOH \\ | \\ CH_2OH \end{array}$$

Gluconic acid $$\begin{array}{c} CO_2H \\ | \\ HCOH \\ | \\ HOCH \\ | \\ HCOH \\ | \\ HCOH \\ | \\ CH_2OH \end{array}$$

Galatonic acid $$\begin{array}{c} CO_2H \\ | \\ HCOH \\ | \\ HOCH \\ | \\ HOCH \\ | \\ HCOH \\ | \\ CH_2OH \end{array}$$

Gulonic acid $$\begin{array}{c} CO_2H \\ | \\ HCOH \\ | \\ HCOH \\ | \\ HOCH \\ | \\ HCOH \\ | \\ CH_2OH \end{array}$$

TABLE II-continued

Glucoheptanoic acid $$\begin{array}{c} CO_2H \\ | \\ HCOH \\ | \\ HCOH \\ | \\ HOCH \\ | \\ HCOH \\ | \\ HCOH \\ | \\ CH_2OH \end{array}$$

The following specific examples are intended to illustrate more fully the nature of the invention without acting as a limitation upon its scope.

EXAMPLE 1

Under a nitrogen atmosphere, $SnCl_2.2H_2O$ (45.2g., 0.2 moles) was added with stirring to 20% NaOH (46 ml) containing D-glucono-δ-lactone (35.6g., 0.2 moles){D-glucono-δ-lactone hydrolyzes to gluconic acid in water}. Additional 20% NaOH (90 Ml) was added to the resulting milky-white solution, followed by the addition of NaOH pellets until the solution became clear. The clear yellowish solution was about 0.9 M (1.8 N) in Sn(II), as determined iodometrically, and had a pH of ~ 13.5. The pH was adjusted to 13.2 by the addition of concentrated hydrochloric acid. The resulting solution, when applied to the skin of the leg effectively removed all hair without irritation within 10 minutes.

EXAMPLE II

Under a nitrogen atmosphere, concentrated ammonium hydroxide (11.5 ml) was added slowly with stirring to a solution of $SnCl_2.2H_2O$ (18.0g, 0.08 moles) in distilled water (42g). The thick, off-white precipitate was suction filtered and washed three times with distilled water. The creamy white solid ($SnO.xH_2O$) was added to a solution of D-glucono-δ-lactone (14.5g, 0.082 moles) in 2.5 M NaOH (65 ml) and distilled water (55 ml). NaOH pellets (1.8g) were added with heating until the solution cleared; the temperature was not allowed to exceed 80° C. The solution was about 0.45 M (0.9 N) in Sn(II) and had a pH between 13.1 and 13.2.

The following stannite compositions were prepared employing the procedure of Example II.

EXAMPLE III

| Ingredient | % by Weight | pH |
|---|---|---|
| Sn(II) hydroxide | 3.6 | 13.1 |
| Gluconic Acid | 3.3 | |
| Sodium hydroxide | 3.5 | |
| Kaolin | 19.7 | |
| Sodium linear alkylate sulfonate (Ultrawet K, ARCO Chemical | 0.1 | |
| $H_2O$ | q.s. to 100 | |

EXAMPLE IV

| Ingredient | % by Weight | pH |
|---|---|---|
| Sn(II) hydroxide | 5.3 | 13.1 |
| Ribonic Acid | 5.3 | |
| Sodium Hydroxide | 5.3 | |
| Octylphenoxypolyethoxyethanol (Triton X-100, Rohm & Haas) | 0.1 | |

-continued

| Ingredient | % by Weight | pH |
|---|---|---|
| H₂O | q.s. to 100 | |

EXAMPLE V

| Ingredient | % by Weight | pH |
|---|---|---|
| Sn(II) hydroxide | 5.5 | 13.1 |
| Glucoheptanoic acid | 6.8 | |
| Sodium hydroxide | 3.0 | |
| Octylphenoxypolyethoxyethanol (Triton X-100, Rohm & Haas) | 0.1 | |
| H₂O | q.s. to 100 | |

EXAMPLE VI

| Ingredient | % by Weight | pH |
|---|---|---|
| Sn(II) hydroxide | 5.7 | 12.8–12.9 |
| Gluconic acid | 5.8 | |
| Sodium hydroxide | 4.7 | |
| Octylphenoxypolyethoxyethanol (Triton X-100, Rohm & Haas) | 0.1 | |
| H₂O | q.s. to 100 | |

Examples III, IV, V and VI are approximately 0.4 molar in Sn(II) hydroxide and have 0.67 molar equivalents of the polyhydroxycarboxylate anion.

Applying the composition of Examples II through IV to the skin resulted in effective depilation in 10 minutes or less with substantially no irritation.

What is claimed is:

1. An aqueous soluble stannite personal care depilatory composition comprising from 0.2 to 0.8 M $Sn^{2+}$ complexed with a member of the group consisting of polyhydroxymonocarboxylate anions of five to seven carbon atoms and of four to six hydroxyl groups, the molar ratio in said composition of $Sn^{2+}$ to said member being from 2:1 to 1:2 and the pH of said composition being from 12.8 to 13.3.

2. An aqueous soluble stannite personal care depilatory as claimed in claim 1 in which the ratio of $Sn^{2+}$ to said member is from 3:2 to 4:3.

3. An aqueous soluble stannite personal care depilatory composition as claimed in claim 1 in which the pH of said composition is from 12.9 to 13.2.

4. An aqueous soluble stannite personal care depilatory composition as claimed in claim 1 in which the concentration of aqueous $Sn^{2+}$ is from 0.3 to 0.5 M.

5. An aqueous soluble stannite personal care depilatory composition as claimed in claim 1 in which said polyhydroxymonocarboxylate anion is gluconate anion.

6. An aqueous soluble stannite personal care depilatory composition comprising from 0.2 to 0.8 M $Sn^{2+}$ complexed with a member of the group consisting of polyhydroxymonocarboxylate anions of five to seven carbon atoms and of four to six hydroxyl groups, and a thickening agent stable at alkaline pH and inert to the substances in said composition, the molar ratio in said composition of $Sn^{2+}$ to said member being from 2:1 to 1:2 and the pH of said composition being from 12.8 to 13.3.

7. An aqueous soluble stannite personal care depilatory composition comprising from 0.2 to 0.8 M $Sn^{2+}$ complexed with a member of the group consisting of polyhydroxymonocarboxylate anions of five to seven carbon atoms and of four to six hydroxyl groups, and a surface active agent selected from the group consisting of anionic, and nonionic, and ampholytic surfactants stable at alkaline pH and inert to the substances in said composition, the molar ratio in said composition of $Sn^{2+}$ to said member being from 2:1 to 1:2 and the pH of said composition being from 12.8 to 13.3.

8. A personal care depilation method comprising the application of an aqueous soluble stannite composition containing $Sn^{2+}$ complexed with a polyhydroxymonocarboxylate anion of five to seven carbon atoms and of four to six hydroxyl groups, the pH of said composition being from 12.8 to 13.3.

* * * * *